United States Patent [19]

Childers-Zadah

[11] Patent Number: 5,786,382

[45] Date of Patent: Jul. 28, 1998

[54] USE OF VALERIAN PLANT AND/OR ROOT AS A SCENT-ATTRACTANT FOR STIMULATING CANINES AND FELINES

[76] Inventor: Vsande Childers-Zadah, 1659 Brandywine #6218, West Palm Beach, Fla. 33409

[21] Appl. No.: 553,037

[22] Filed: Nov. 3, 1995

[51] Int. Cl.[6] .................................................. A01N 37/18
[52] U.S. Cl. ...................... 514/629; 514/253; 514/278; 514/283; 514/320; 514/923
[58] Field of Search .................................. 514/629, 923, 514/320, 283, 253, 278

[56] References Cited

U.S. PATENT DOCUMENTS 5,506,268   4/1996   Balandrin et al. .................. 514/629

FOREIGN PATENT DOCUMENTS 0724832   8/1996   European Pat. Off. .

OTHER PUBLICATIONS

Johnson, R.D.; Waller, G.R. Phytochemistry (1971) Isolation of Actinidine from Valeriana Officinalis 10(12) pp. 3334-3335 (1971).

Primary Examiner—Terressa Mosley

[57] ABSTRACT

Use of the herb/plant Valerian, in all of its forms, whether whole or in part; powdered, chopped, ground, or "tea"; the root and that portion which grows above ground; in toys; food-products; and medications (though not limited to the preceding applications); and in such manner that the natural aroma emitted by the Valerian plant will act as a powerful new scent-attractant for canines and/or felines.

7 Claims, 6 Drawing Sheets

USE OF VALERIAN PLANT AND/OR ROOT AS A SCENT-ATTRACTANT FOR STIMULATING CANINES AND FELINES

BACKGROUND OF INVENTION

1. Field of Invention

This invention relates to scent-attractants, specifically to such scent-attractants which are used in pet toys, food-products, and medications as a means of enticing and exciting canines and/or felines.

2. Description of Prior Art

Veterinarians, pet-supply stores and distributors, drug stores, and grocery stores commonly sell medications, toys, and foods designed and manufactured for household pets, and the vast majority of these products utilizes scent-attractants.

For decades, the primary scent-attractants in use have been catnip, and meat, fish, and poultry derivatives/imitations. However, consumers are constantly searching for new products which will a) encourage their pets to take medications; and/or b) encourage their pets to eat a particular food-product; and/or c) provide enjoyment for their pets; and/or d) provide a new means of interacting with their pets.

Although catnip has become a "standard" in the pet industry, a) catnip has absolutely no effect on canines and is not used in products created for dogs; and b) catnip does not have as dramatic an effect upon cats as does the Valerian Plant and/or the Valerian Root. In addition, there is no herb presently being used as a catnip-equivalent for dogs.

Furthermore, the success of scent-attractants replicating meat, fish, and poultry scents is dependent upon various factors, including (but not limited to) each animal's diet after weaning, personal tastes, and owner's decisions regarding foods and brands. Applicant's testing reveals, however, that the majority of dogs and cats is biologically predisposed towards an extraordinarily dramatic and positive reaction to the Valerian Plant and/or the Valerian Root.

Sugary and/or otherwise sweetened flavorings are also used to increase palatability, and a great number of pet-owners feel that this is not healthy for their animals. The Valerian Plant and the Valerian Root are much healthier, non-toxic, and the only "side-affect" is as a mild sedative when administered in quantities significantly larger than those directed for use in this patent application.

SUMMARY OF INVENTION

In conducting the patent search, Applicant discovered many patents for scent-attractants [CL 119—Animal Husbandry; Sub-class 711—Toys], though none which mentioned either the Valerian Plant nor the Valerian Root in any way, shape, or form. The only Valerian-related patent discovered by the Applicant was U.S. Pat. No. 5,211,948, issued in 1993, Assignee Code 397085, Classification 424/195.1 and 426/3, entitled "Process for the Preparation of a Powdered Extract of Valerian Roots".

In addition, Applicant had never read anything published about this phenomenon [animals' intense attraction to the scent of the Valerian Plant and/or the Valerian Root, and/or the extreme excitation as a reaction to its aroma] during years of research on herbs, and in more than thirty years of using this herb. It was not until Applicant made the mistake of leaving it on a counter to be discovered by Applicant's cat that said Applicant began testing it with animals. Recently, Applicant met someone who told a personal anecdote about their own cat finding their Valerian Root and "going crazy", but it is such an uncommon herb that few have even heard of it.

Scientific research has been done regarding the sedative properties of Valerian. No mention is made of Valerian's "catnip-like" qualities, for dogs, cats, nor for any other animals.

Accordingly, to clarify the use of the Valerian Plant and/or the Valerian Root as a Scent-Attractant for Canines and/or Felines as stated above, several objects and advantages of the present invention are:

a) to provide new, natural, and safe products which elicit dramatic and positive responses from both cats and dogs;

b) to provide new, natural, and safe products, which elicit dramatically positive responses from both cats and dogs, yet are not reliant on meat, meat by-products, catnip, and/or sweeteners;

c) to provide, new, natural, and safe products which create a solution to the problems occurring when pets resist taking prescribed medications;

d) to provide new, natural, safe toys which create greater excitement and add more enjoyment, for both pets and pet-owners, during playtime;

e) to provide new, natural, and safe pet food-treats which would elicit such a strong response from cats and dogs that they would prove extremely effective as incentives and/or rewards during training sessions, in addition to being used as "treats".

BRIEF DESCRIPTION OF DRAWINGS

In the Applicant's drawings, closely-related figures have the same number, but different alphabetic suffixes.

Figure 1A:
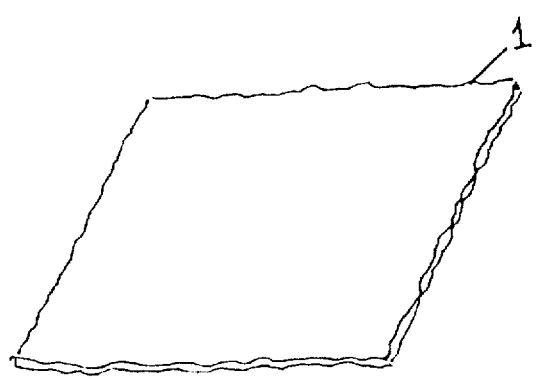
FIGS. 1A–1E show various aspects of one method of creating a "chew toy".
Figure 1B:
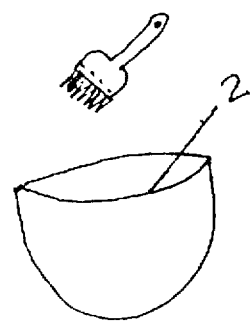
Figure 1C:
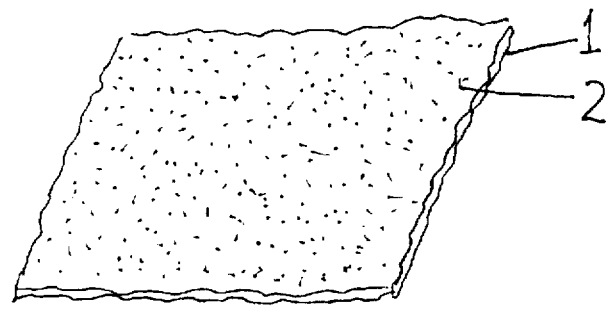
Figure 1D:
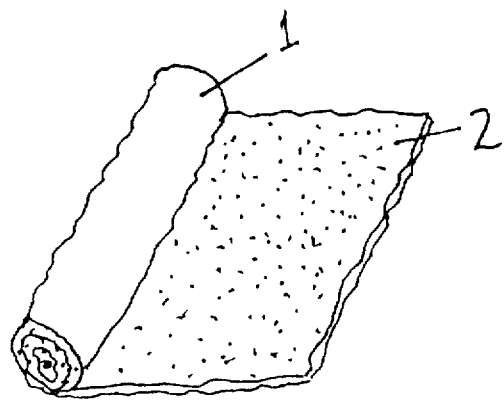
Figure 1E:
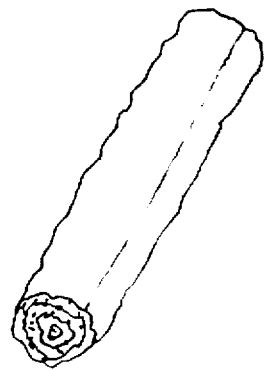
Figure 2A:
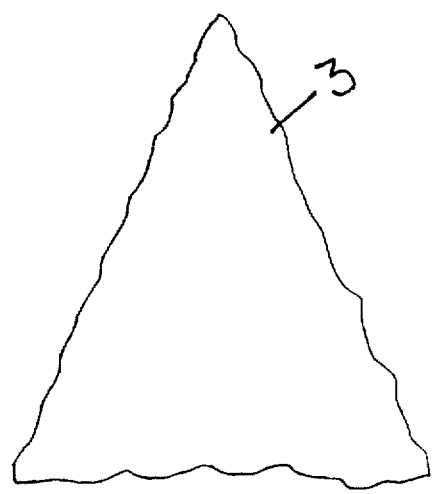
FIGS. 2A–2E show various aspects of one method of creating a "chew toy".
Figure 2B:
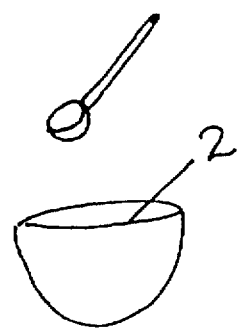
Figure 2C:
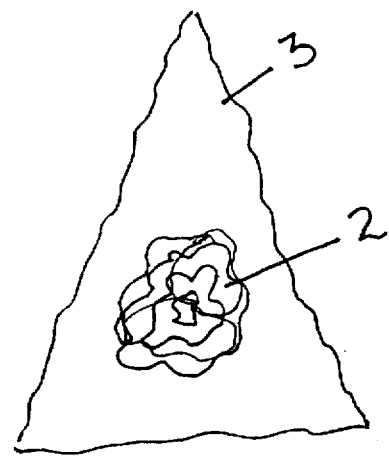
Figure 2D:
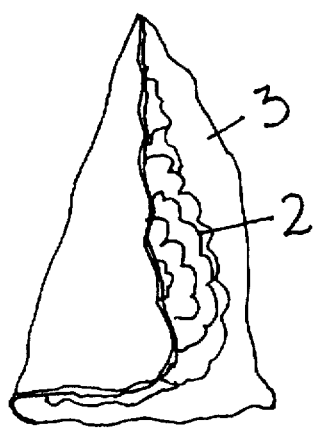
Figure 2E:
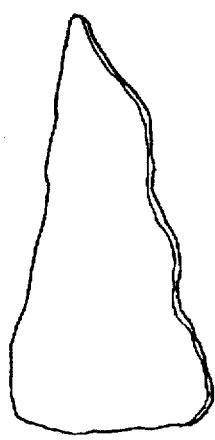
Figure 3A:
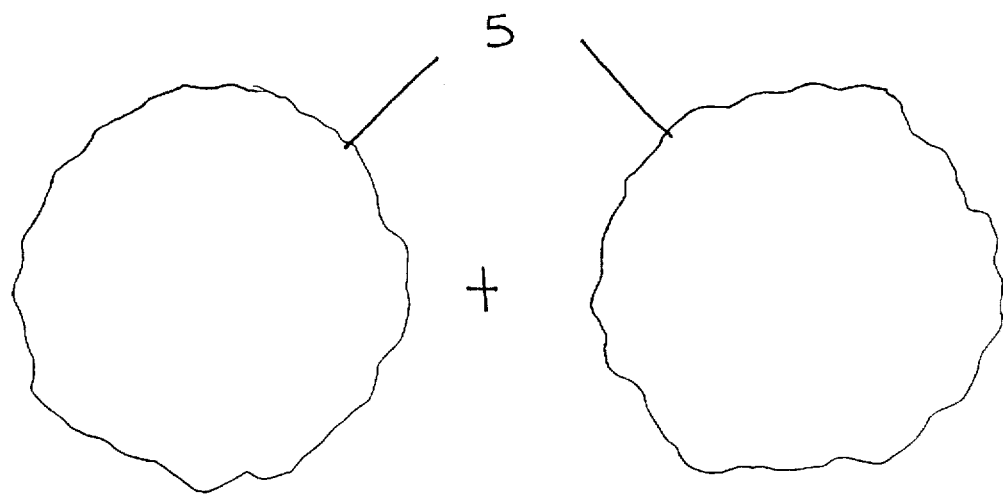
FIGS. 3A–3D show various aspects of one method of creating a cloth toy.
Figure 3B:
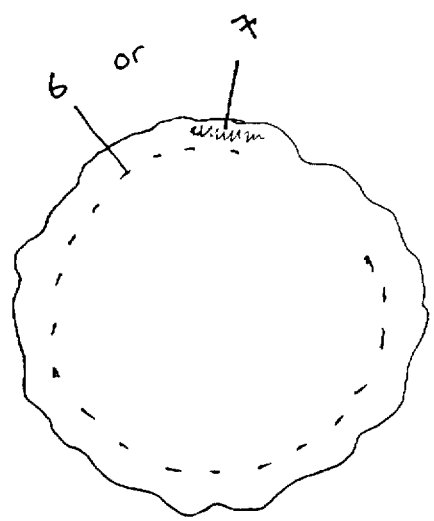
Figure 3C:
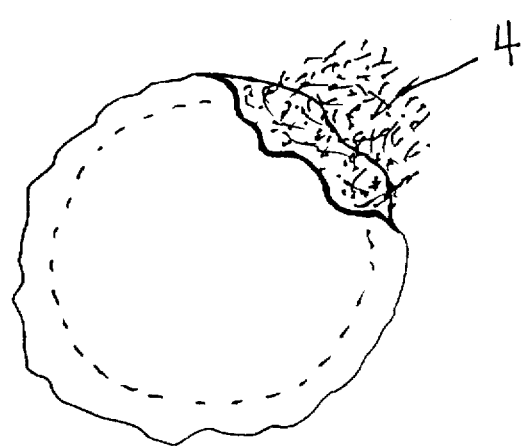
Figure 3D:
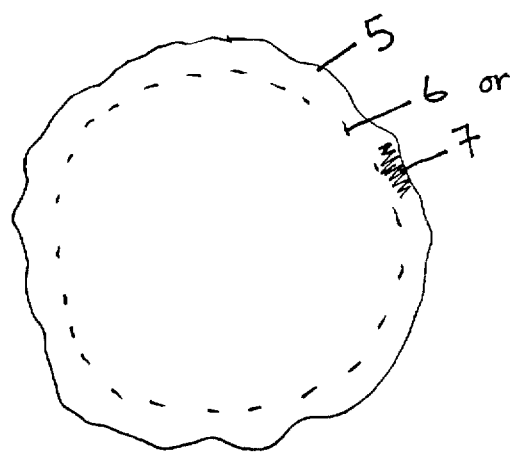
Figure 4A:
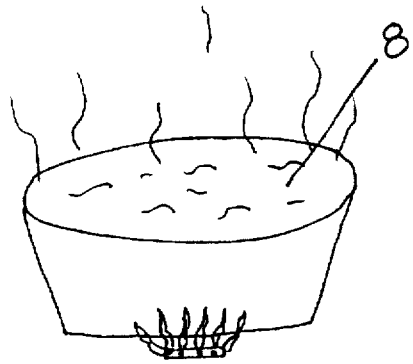
FIGS. 4A–4F show various aspects of one method of creating a "chew toy".
Figure 4B:
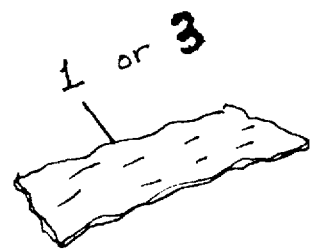
Figure 4C:
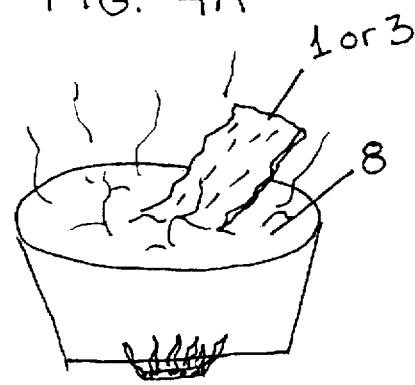
Figure 4D:
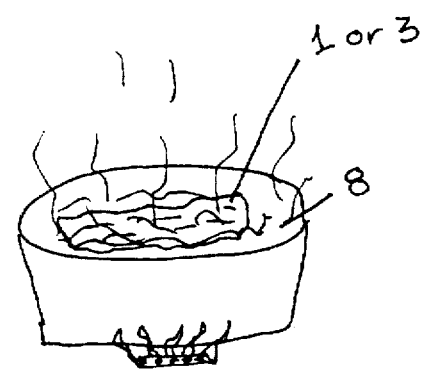
Figure 4E:
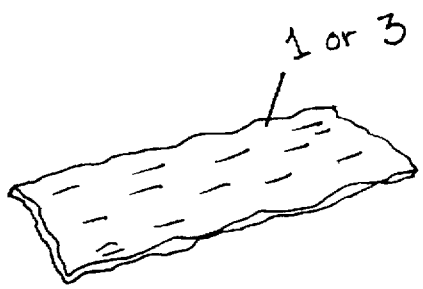
Figure 4F:
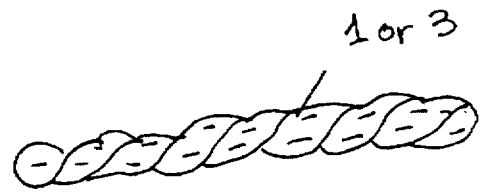

Explanation of Reference Numerals Used in Drawings

1 Rawhide (rectangular, pre-treated, not dried) or equivalent/substitute
2 Valerian Paste
3 Pig's Ear (pre-treated though not dried) or equivalent/substitute
4 Valerian Tea Leaves (or substitute filler) Mixed with Valerian Root Powder
5 Cloth
6 Stitching/Thread
7 Valerian Tea Leaves
8 Gel Capsule (or equivalent/substitute)
9 Valerian Root Powder

DETAILED DESCRIPTION OF INVENTION [DESCRIPTION OF THE PREFERRED EMBODIMENT]

Accordingly, Use of the Valerian Plant and/or Root as a Scent-Attractant for Canines and/or Felines can be employed to greater advantage than other scent-attractants in that a) most dogs and cats are biologically pre-disposed to an intensely powerful and instinctive attraction to Valerian;

b) it is the only herb which has shown such drastic effect on both dogs and cats;

c) it is a naturally occurring non-toxic, non-addictive, "cruelty-free", unsweetened substance, and its only side-effect is as a mild sedative when administered in quantities significantly greater than those recommended in the recipes above;

d) it is relatively inexpensive and easily available (if one knows where to look);

e) it increases the animals' desire to play, and helps them get more exercise;

f) the use of Valerian provides endless (and inexpensive) entertainment for those who own canines and/or felines;

g) the use of the Valerian Plant and/or Valerian Root as a Scent-Attractant decreases canines' and felines' resistance to accepting oral medications;

h) toys and treats containing Valerian are a powerful training tool.

Although the above description contains many specifics, these should not be construed as limiting the scope of the Applicant's invention, but simply as providing illustrations of some of the presently preferred embodiments of using the Valerian Plant and/or Valerian Root as a Scent-Attractant. For example, toys can be made any shape and/or size, and from a wide variety of natural and/or synthetic materials. Thus the scope of Applicant's invention should be determined by the appended claims and their legal equivalents rather than by the examples given, herein.

A typical method for creating a "chew toy" using Applicant's scent-attractant is illustrated in FIGS. 1A through 1E. First, a rectangular piece of rawhide or equivalent/substitute [1] is laid flat. Next, a thin layer (approximately 3 centimeters deep) of the Valerian Paste [2] (created, most commonly, by using a mixture that is ¾ [75%] dry, pet-food glazing-compound to ¼ [25%] Valerian Root Powder [9], and then adding small amounts of water, stirring constantly until a thick paste has been achieved) is spread completely across the flat piece of rawhide. Lastly, the rawhide is rolled (in a manner much like storing a sleeping-bag), and left to dry. Once dried, this is an exciting, long-lasting, and healthy pet-toy.

A typical method for creating a "chew toy" using Applicant's scent-attractant is illustrated in FIGS. 2A through 2E. First, a pig's ear or equivalent substitute [3] is laid flat (it will appear triangular). Next, a "heaping tablespoon" of the Valerian Paste [2; see recipe above] is placed in the center of the ear. Then, the pig's ear is folded over and gently "squished" until it forms a smaller triangle with a large lump in the middle (looking much like an East Indian "samosa"), and the sides are held together, firmly, by the Valerian Paste mixture. Lastly, the toy is left to dry, after which, one has created an exciting, long-lasting, natural, and healthy pet-toy.

A typical method for creating a toy using Applicant's scent-attractant is illustrated in FIGS. 3A through 3D. First, two similarly shaped pieces of cloth [5] are cut and laid flat. Secondly, a portion of the Valerian Tea Leaf and Powder Mixture [4] (which is generally prepared using 8 ounces of Valerian Root Powder [9] per each 1 pound of Valerian Tea Leaves [7; creating a mixture which is 33.33% Valerian Root Powder and 66.66% Valerian Tea Leaves], although other fillers may be substituted for the Valerian Tea Leaves) is placed in the center of one of the pieces of fabric, and then covered by the other piece of fabric. The two pieces are then sewn [6] (or glued) together, encasing the Valerian mixture. To reduce potency, use the same proportions of Valerian Root Powder to any other grass, tea (catnip may be also substituted for the Valerian Tea Leaves). This creates an exciting, natural, and healthy new toy for canines and/or felines.

A typical method for creating a "chew toy" using Applicant's scent-attractant is illustrated in FIGS. 4A through 4F. Firstly, in a container suitable for extended periods of boiling at high temperatures, place one cup of Valerian Tea Leaves [7] for each 1 gallon of water used (a ratio of 1 part Valerian Tea Leaves per 16 parts water). Bring to a rapid boil. Then add rectangular strips of rawhide or equivalent/substitute [1], or pig's ears or equivalent/substitute [3] to the boiling Valerian Tea. Continue boiling, depending upon desired strength, for 20 minutes to several hours (if shorter boiling periods are used, the Valerian Tea mixture may be re-used two or three times). After boiling process is completed, remove articles from Valerian Tea, twist, then dry. This creates an exciting, natural, healthy, and long-lasting pet-toy.

Figure 5:
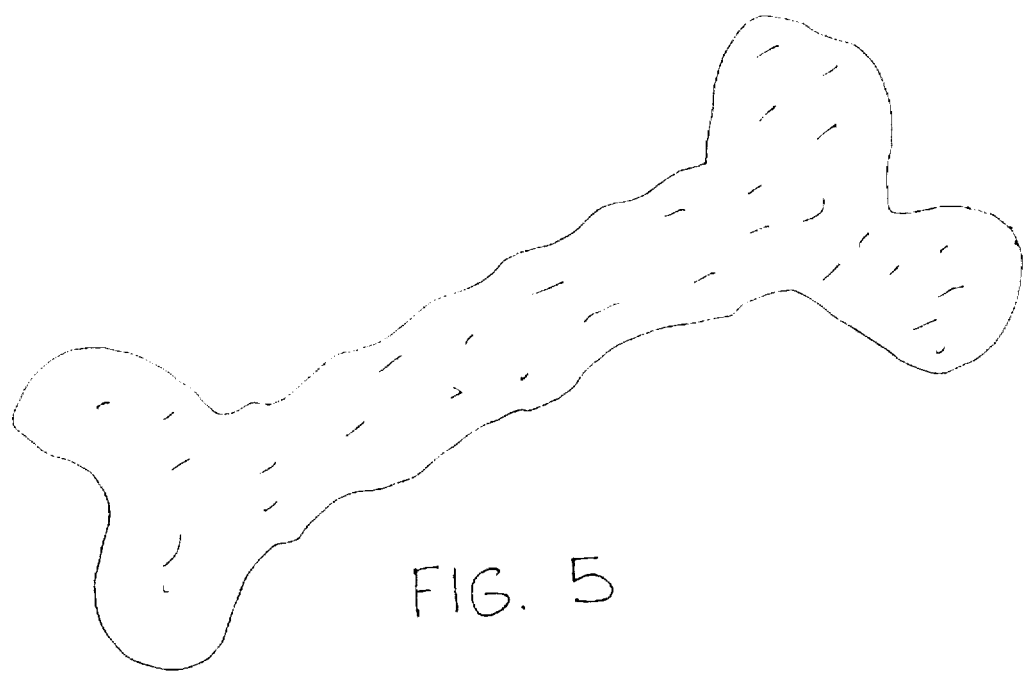
FIGS. 5 and 6 show two types of baked and/or pressed food "treats".

A typical method for creating a large "pet-food treat" using Applicant's scent-attractant is illustrated in FIG. 5. Using a standard "big treat" recipe, simply replace a portion of an inactive, dry ingredient with the same amount of Valerian Root Powder [9], or simply add Valerian Root Powder plus a tiny amount of additional liquid. Recipes are best when the amount of Valerian Root Powder is equal to ⅛ [12%] of the total amount of dry ingredients per batch. "Treats" are then pressed and/or baked, as per the usual instructions. This creates an exciting, large, natural, and healthy "pet treat".

Figure 6:
Figure 6:
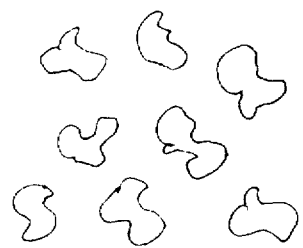

A typical method for creating bite-sized "pet-food treats" using Applicant's scent-attractant is illustrated in FIG. 6. Using a standard "treat" recipe, simply replace a portion of an inactive, dry ingredient with the same amount of Valerian Root Powder [9], or simply add Valerian Root Powder plus a tiny amount of additional liquid. Recipes are best when the amount of Valerian Root Powder is equal to ⅛ [12%] of the total amount of dry ingredients per batch. "Treats" are then pressed and/or baked, as per the usual instructions. This creates exciting, bite-sized, natural, and healthy "pet treats".

Figure 7A:
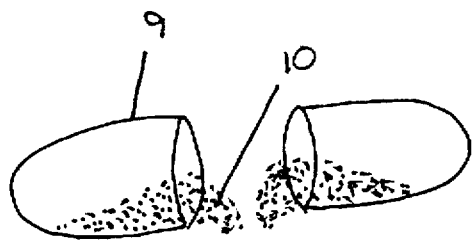
FIGS. 7A and 7B show various aspects of one method of creating encapsulated medications.
Figure 7B:
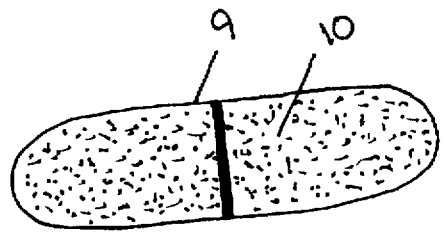

A typical method for creating medications more easily accepted by canines and felines, using Applicant's scent-attractant is illustrated in FIGS. 7A and 7B. Using a gel-capsule [8], replace inactive/inert/filler ingredients from medication-mixtures with exactly the same amount of Valerian Root Powder [9]. Fill capsules and then close. This creates a capsule of medicine which is much more palatable to dogs and cats than regularly produced medications.

Figure 8:
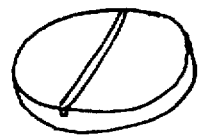
FIG. 8 shows one type of pressed and/or molded pill-form used for giving medications.

A typical method for creating medications more easily accepted by canines and felines, using Applicant's scent-attractant is illustrated in FIG. 8. When manufacturing standard pills, simply replace the filler agent with exactly the same amount of Valerian Root Powder [9], then press into pill form. This creates medication in pill form which is much more palatable to dogs and cats than regularly produced medications.

I claim:

1. A method of inducing and/or stimulating the interest, attention, and appetite of a canine and/or feline comprising adding an effective amount of Valerian plant and/or root to ingredients used in the manufacture of ingestible and/or non-ingestible products wherein the amount of Valerian equals no less than 12.5% and no more than 50% of the total weight of dry ingredients when in powder form and/or wherein the amount of Valerian equals no less than 25% and no more than 75% of the total weight of dry ingredients when in Valerian plant form and/or wherein the amount of Valerian equals no less than 25% and no more than 100% of the dry ingredients when in the form of an aqueous extract, such that the aroma of Valerian acts as a stimulant and excitement-producing scent-attractant for canines and/or felines.

2. A method of inducing and/or stimulating the interest, attention, and appetite of a canine and/or feline comprising adding an effective amount of Valerian plant and/or root to ingredients used in the manufacture of food products wherein the amount of Valerian equals no less than 3% and no more than 12.5% of the total weight of dry ingredients when in powder form and/or wherein the amount of Valerian equals no less than 3% and no more than 25% of the total weight of dry ingredients when in Valerian plant form and/or wherein the amount of Valerian equals no less than 25% and no more than 100% of the total weight of dry ingredients when in the form of an aqueous extract, such that the aroma of Valerian acts as a stimulant and excitement-producing scent-attractant for canines and/or felines as dependent upon claim 1.

3. A method of inducing and/or stimulating the interest, attention, and appetite of a canine and/or feline comprising adding an effective amount of Valerian plant and/or root to rawhide, pigs' ears, and/or other ingestible and/or non-ingestible equivalents thereof wherein the amount of Valerian equals no less than 5% and no more than 50% of the total weight of dry ingredients when in powder form and/or wherein the amount of Valerian equals no less than 12.5% and no more than 75% of the total weight of dry ingredients when in Valerian plant form and/or wherein the amount of Valerian equals no less than 25% and no more than 100% of the total weight of dry ingredients when in the form of an aqueous extract, such that the aroma of Valerian acts as a stimulant and excitement-producing scent-attractant for canines and/or felines as dependent upon claim 1.

4. A method of inducing and/or stimulating the interest, attention, and appetite of a canine and/or feline comprising adding an effective amount of Valerian plant and/or root to non-ingestible toys wherein the amount of Valerian equals no less than 5% and no more than 50% of the total weight of dry ingredients when in powder form and/or wherein the amount of Valerian equals no less than 12.5% and no more than 75% of the total weight of dry ingredients when in Valerian plant form and/or wherein the amount of Valerian equals no less than 25% and no more than 100% of the total weight of dry ingredients when in the form of an aqueous extract, such that the aroma of Valerian acts as a stimulant and excitement-producing scent-attractant for canines and/or felines as dependent upon claim 1.

5. A method of inducing and/or stimulating the interest, attention, and appetite of a canine and/or feline comprising adding an effective amount of Valerian plant and/or root to ingredients used in the manufacture of edible treats wherein the amount of Valerian equals no less than 3% and no more than 12.5% of the total weight of dry ingredients when in powder form and/or wherein the amount of Valerian equals no less than 3% and no more than 25% of the total weight of dry ingredients when in Valerian plant form and/or wherein the amount of Valerian equals no less than 25% and no more than 100% of the dry ingredients when in the form of an aqueous extract, such that the aroma of Valerian acts as a stimulant and excitement-producing scent-attractant for canines and/or felines as dependent upon claim 1.

6. A method of inducing and/or stimulating the interest, attention, and appetite of a canine and/or feline comprising adding an effective amount of Valerian plant and/or root to a coating compound wherein the amount of Valerian is equal to no less than 12.5% and no more than 100% of the total dry weight of ingredients when in powder form and/or wherein the amount of Valerian equals no less than 25% and no more than 200% of the total weight of dry ingredients when in Valerian plant form and/or wherein the amount of Valerian equals no less than 25% and no more than 200% of the total weight of dry ingredients when in the form of an aqueous extract, such that the coating compound can be utilized in the manufacture of ingestible and non-ingestible products and the aroma of Valerian acts as a stimulant and excitement-producing scent-attractant for canines and/or felines as dependent upon claim 1.

7. A method of inducing and/or stimulating the interest, attention, and appetite of a canine and/or feline comprising adding an effective amount of Valerian to water heated to a temperature of 100° Celsius wherein the amount of Valerian in plant form, powder form, and/or the form of an aqueous extract is equal to no less than 12.5% and no more than 75% by volume of the amount of water, and wherein the resulting mixture is continuously heated at a temperature of no less 60° Celsius and no more than 100° Celsius under atmospheric pressure for no less than 10 minutes and no more than five hours, continuing to add water as necessary such that the resulting aqueous solution adds the Valerian aroma to toys and/or foods and/or other ingestible and non-ingestible products and such that aroma of Valerian acts as a stimulant and excitement-producing scent-attractant for canines and/or felines as dependent upon claim 1.

* * * * *